United States Patent [19]

Bender

[11] Patent Number: 5,707,234
[45] Date of Patent: Jan. 13, 1998

[54] CARTRIDGE FOR DISPENSING DENTAL MATERIAL

[75] Inventor: Dieter Bender, Konstanz, Germany

[73] Assignee: Dentsply G.m.b.H., Dreieich, Germany

[21] Appl. No.: 449,460

[22] Filed: May 24, 1995

[51] Int. Cl.$^6$ .................................................... A61C 5/04
[52] U.S. Cl. .................................................... 433/90; 433/82
[58] Field of Search ................................ 433/82, 83, 87, 433/89, 90, 80

[56] References Cited

U.S. PATENT DOCUMENTS

| | | | |
|---|---|---|---|
| 2,505,028 | 11/1950 | Boeger | 128/215 |
| 2,825,134 | 3/1958 | Hicks | 433/90 |
| 2,847,009 | 5/1958 | Blease | 128/222 |
| 3,164,303 | 1/1965 | Trautmann | 222/190 |
| 3,581,399 | 6/1971 | Dragan | 32/60 |
| 3,900,954 | 8/1975 | Dragan | 32/60 |
| 3,917,062 | 11/1975 | Winters | 206/219 |
| 4,198,756 | 4/1980 | Dragan | 222/326 |
| 4,330,280 | 5/1982 | Dougherty et al. | 433/90 |
| 4,384,853 | 5/1983 | Welsh | 433/90 |
| 4,391,590 | 7/1983 | Dougherty | 433/90 |
| 4,479,781 | 10/1984 | Herold et al. | 433/90 |
| 4,693,706 | 9/1987 | Ennis, III | 604/87 |
| 4,969,816 | 11/1990 | Drumm | 433/89 |
| 5,172,807 | 12/1992 | Dragan et al. | 433/90 X |
| B1 4,384,853 | 5/1983 | Welsh | 433/90 |
| B1 4,391,590 | 7/1983 | Dougherty | 433/90 |

FOREIGN PATENT DOCUMENTS

| | | |
|---|---|---|
| 0 063 891 | 4/1982 | European Pat. Off. . |
| 0 145 922 | 4/1982 | European Pat. Off. . |
| 0 382 481 | 8/1990 | European Pat. Off. . |
| 3930817 | 3/1990 | Germany ............. 433/90 |

OTHER PUBLICATIONS

Glass–Ionomer Restaurative Material; De Trey Division, Dentsply Limited; Weybridge, Surrey, England.

Primary Examiner—Christopher A. Bennett
Attorney, Agent, or Firm—Dale R. Lovercheck; James B. Bieber

[57] ABSTRACT

The invention provides a miniature capsule-like cartridge having a hollow elongated generally cylindrical body having an inner wall with a substantially uniform diameter. The inner wall encloses a chamber. One end of the body is open and formed at the extremity thereof with an annular circular exterior flange. The opposite end of the body is closed by an end wall. A discharge nipple integrally connected to the body and has a passageway therethrough extending from the chamber at the closed end of the body to facilitate discharge of a polymerizable dental composition from the cartridge. The nipple has an outer wall. The outer wall has a proximal diameter proximal to the body and a medial diameter at a medial position along the central axis of the nipple and medial to the body. The medial diameter is greater than or equal to the proximal diameter. A cup-shaped cap is removably connected to the discharge nipple on the body to close the opening of the passageway at the outer end of the nipple. The cap extends over the medial position of the nipple.

12 Claims, 4 Drawing Sheets

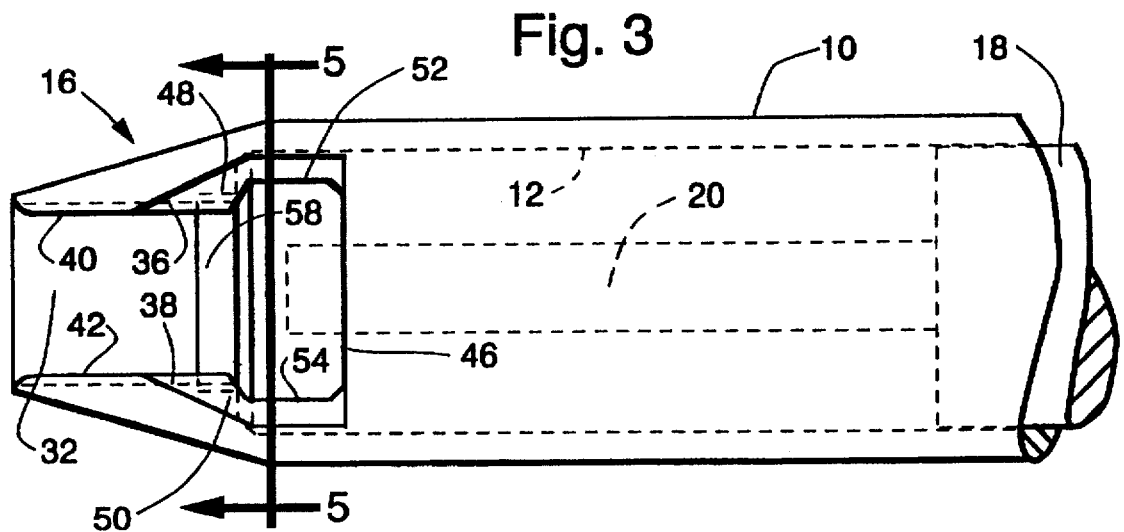
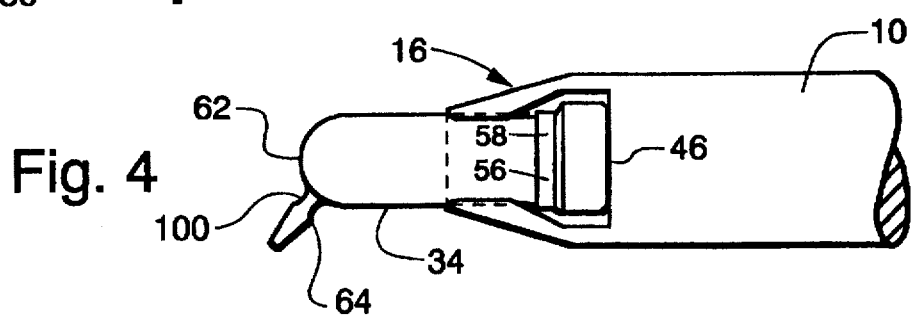
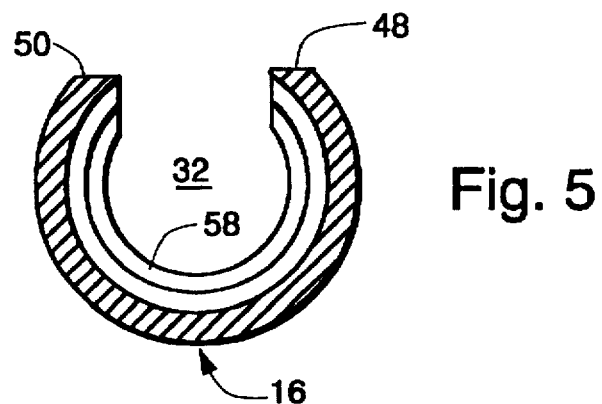
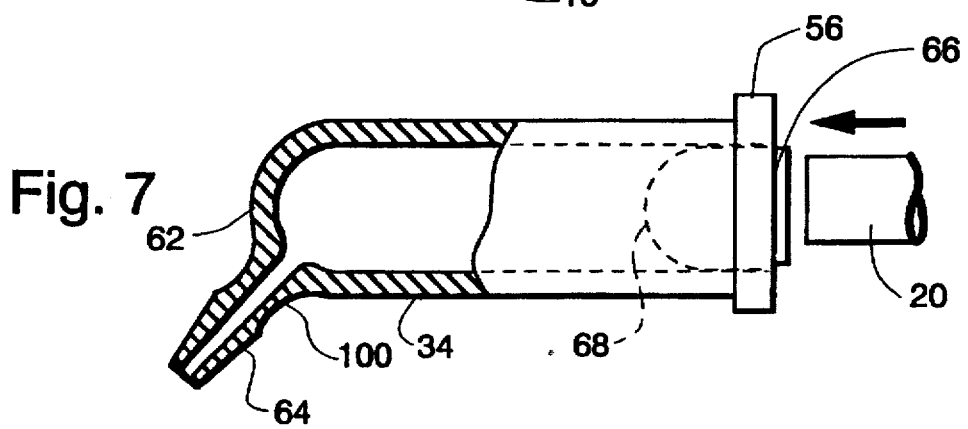

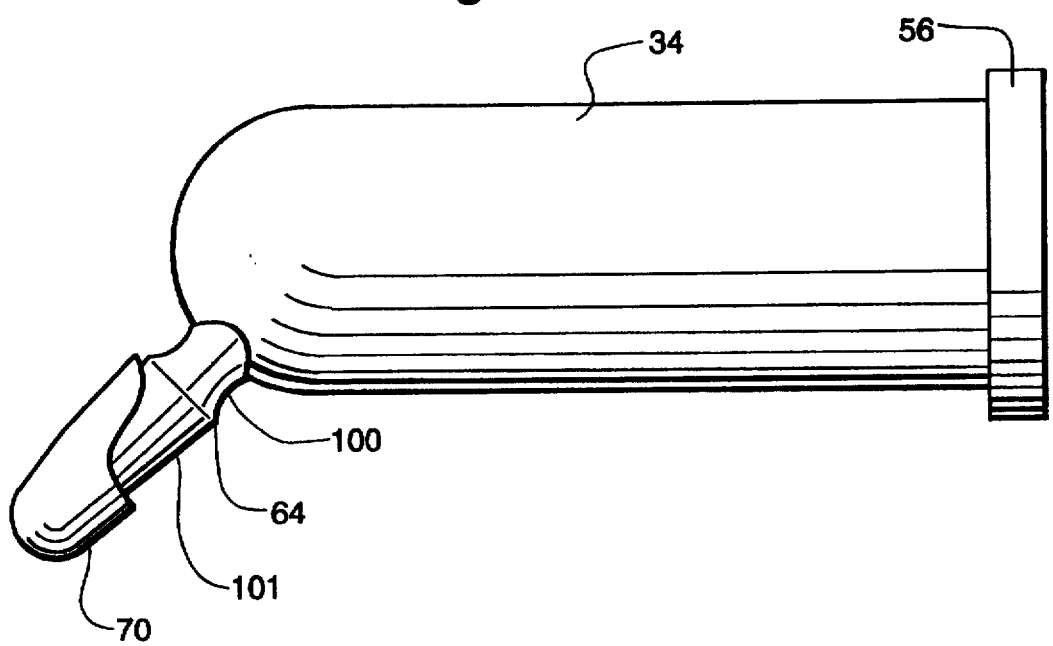
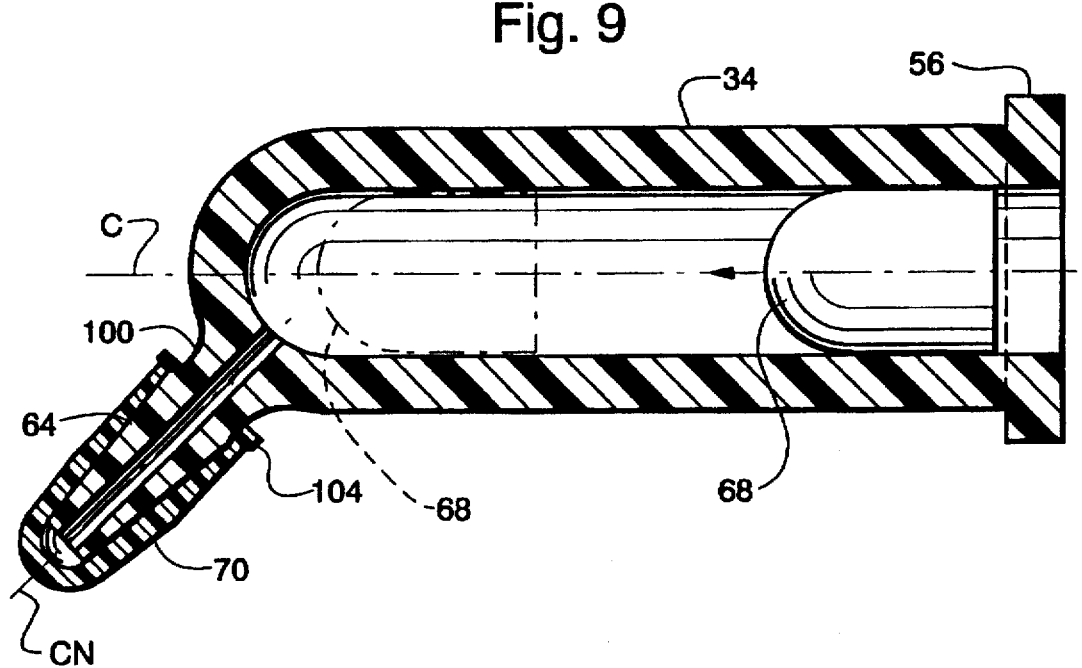

CARTRIDGE FOR DISPENSING DENTAL MATERIAL

The invention relates to cartridges of dispensing dental material. An improved cartridge of dispensing dental material is provided in accordance with the invention.

BACKGROUND OF THE INVENTION

Cruttenden in U.S. Pat. No. 716,676 discloses dental cement injector. Kelley in U.S. Pat. No. 742,446 discloses dental filling tool. Skinner in U.S. Pat. No. 921,015 discloses root canal filling dental injector. Dalbey in U.S. Pat. No. 1,188,417 discloses dental instrument. Sprague in U.S. Pat. No. 1,775,329 discloses applicator. Howard in U.S. Pat. No. 1,306,816 discloses syringe for injecting cement in teeth. Hagemeier in U.S. Pat. No. 2,102,591 discloses dental syringe. Rutrough in U.S. Pat. No. 2,251,206 discloses amalgam carrier. Boeger U.S. Pat. No. 2,505,028 discloses syringe for applying heat-fluent impression composition to dental inlay preparations and the like, and impression-material cartridge for use therein. Cohen in U.S. Pat. No. 2,708,438 discloses hypodermic syringe. Cohen in U.S. Pat. No. 2,754,590 discloses container for toothache remedy. Moller in U.S. Pat. No. 2,837,824 discloses amalgam carrier and ejector. Epps in U.S. Pat. No. 2,841,145 discloses syringe. Blease in U.S. Pat. No. 2,847,009 discloses dispensing liquids. Ratcliff et al. in U.S. Pat. No. 2,869,543 discloses injector. Silver et al. in U.S. Pat. No. 3,052,239 discloses disposable hypodermic syringe. Silver et al. in U.S. Pat. No. 3,052,240 discloses disposable hypodermic syringe. Dunmire in U.S. Pat. No. 3,089,489 discloses aspirating type hypodermic syringes. Everett in U.S. Pat. No. 3,093,133 discloses hypodermic apparatus. Nielsen in U.S. Pat. No. 3,098,483 discloses two-compartment hypodermic syringe for separate storing of more components. Via, Jr. in U.S. Pat. No. 3,100,045 discloses mixing containers. Trautmann in U.S. Pat. No. 3,164,303 discloses storage and mixing cartridge. McConnaughey et al. in U.S. Pat. No. 3,220,412 discloses holder for hypodermic syringe cartridges. Sarnoff et al. in U.S. Pat. No. 3,326,215 discloses two compartment syringe with vapor seal between compartments. Saffir in U.S. Pat. No. 3,373,743 discloses disposable hypodermic syringe. Blank et al. in U.S. Pat. No. 3,417,971 discloses mixing and ejection tool. Shaw in U.S. Pat. No. 3,477,432 discloses combination mixing and injecting medical syringe. Zackheim in U.S. Pat. No. 3,494,359 discloses two compartment syringe with a single barrel. Newman in U.S. Pat. No. 3,521,356 discloses dispenser for dental filling material. Sly in U.S. Pat. No. 3,534,735 discloses disposable injector and holder. Cohen in U.S. Pat. No. 3,557,787 discloses disposable syringe. Kunz in U.S. Pat. No. 3,575,318 discloses water pistol. Dragan in U.S. Pat. No. 3,581,399 discloses composite resin filling syringe and technique. Smith in U.S. Pat. No. 3,612,352 discloses amalgam cartridge and method of making same and method and apparatus for dispensing amalgam from a cartridge. Lopez et al. in U.S. Pat. No. 3,638,314 discloses amalgam carrier and dispenser with preload capsule. Baumann in U.S. Pat. No. 3,684,136 discloses receptacle having a dividing wall. Preston et al. in U.S. Pat. No. 3,724,077 discloses mixing syringe. Lopez et al. in U.S. Pat. No. 3,738,066 discloses dental impression material injecting syringe. Baumann et al. in U.S. Pat. No. 3,739,947 discloses storing and mixing receptacle. Winberg in U.S. Pat. No. 3,756,571 discloses mixing capsule in particular for dental preparation. Mosch in U.S. Pat. No. 3,828,434 discloses mixing capsule. Gardella et al. in U.S. Pat. No. 3,831,742 discloses dental mixing capsule. Nielsen in U.S. Pat. No. 3,890,713 discloses dental devices. Dragan in U.S. Pat. No. 3,900,954 discloses dental filling gun and nozzle tip therefor. Winters in U.S. Pat. No. 3,917,062 disclose mixing container for dental materials. Warden et al. in U.S. Pat. No. 3,951,387 discloses cartridge for storing and mixing at least two independent ingredients. Claasen in U.S. Pat. No. 4,023,675 discloses packing for impression material for dental use. Skeirik in U.S. Pat. No. 4,084,320 discloses system for mixing and dispensing dental amalgam. Dragan in U.S. Pat. No. 4,189,756 discloses manual extruder. Dougherty et al. in U.S. Pat. No. 4,330,280 discloses ejector holder for capsule-like cartridge. Welsh in U.S. Pat. No. B1 4,384,853 disclose ejector holder for capsule-like cartridge. Dougherty in U.S. Pat. Nos. 4,391,590 and B1 4,391,590 disclose cartridge for viscous material. Hofmann-Igl in U.S. Pat. No. 4,392,590 discloses eye drop dispensing bottle. Ennis, III in U.S. Pat. No. 4,693,706 disclose two compartment mixing syringe. Drumm in U.S. Pat. No. 4,969,816 disclose dental material carrier and applicator.

Various types of material, especially medicinal or quasi-medicinal types are often packaged in sealed cartridges, insertable in a suitable type of holder and/or ejector device, for purposes of preserving purity of the medicament and the like, insuring a patient of accurately measured quantities, as well as minimizing effort now required in introducing bulk amounts of material into a syringe and ejecting measured quantities thereof, for example. Various previous efforts in this direction are illustrated and described in various prior U.S. patents, particularly U.S. Pat. Nos. 3,581,399 and 3,900,954 to Dragan, dated Jun. 1, 1971, in which a typical example of loaded cartridge is illustrated in conjunction with one type of holder and discharge device.

It is an object of the present invention to provide a cartridge having a hollow elongated uniformly cylindrical body with an open end and an opposite closed end, and a discharge nipple having a cap with improved retention thereon.

It is an object of the present invention to provide a cartridge having a hollow elongated uniformly cylindrical body with an open end and an opposite closed end, and a discharge nipple having a wall outer surface having a proximal diameter proximal to the body which is greater than its medial diameter.

It is an object of the invention to provide a cartridge having a hollow elongated uniformly cylindrical body with an open end and an opposite closed end, and a discharge nipple having a wall outer surface having a proximal diameter proximal to the body which is greater than its medial diameter medial to the body wherein the body encloses a polymerizable dental composition.

Details of the foregoing objects and of the invention, as well as other objects thereof, are set forth in the following specification and illustrated in the accompanying drawings comprising a part thereof.

BRIEF DESCRIPTION OF THE INVENTION

The invention provides a miniature capsule-like cartridge having a hollow elongated generally cylindrical body having an inner wall with a substantially uniform diameter. The inner wall encloses a chamber. One end of the body is open and formed at the extremity thereof with an annular circular exterior flange. The opposite end of the body is closed by an end wall. A discharge nipple integrally connected to the body and has a passageway therethrough extending from the chamber at the closed end of the body to facilitate discharge of a polymerizable dental composition from the cartridge. The nipple has an outer wall. The outer wall has a proximal diameter proximal to the body and a medial diameter at a medial position along the central axis of the nipple and medial to the body. The medial diameter is greater than or equal to the proximal diameter. A cup-shaped cap is removably connected to the discharge nipple on the body to close the opening of the passageway at the outer end of the nipple. The cap extends over the medial position of the nipple.

BRIEF DESCRIPTION OF THE DRAWINGS

FIG. 3 is a fragmentary enlarged bottom plan view of the forward end of the barrel of the ejector holder shown in FIGS. 1 and 2.

FIG. 4 is a fragmentary bottom plan view of the ejector holder similar to FIG. 3, but on a smaller scale, and illustrating a cartridge supported in the forward end of the barrel.

FIG. 5 is a vertical sectional view of the forward end portion of the barrel of the ejector holder shown in FIG. 3, as seen on the line 5—5 thereof.

FIG. 7 is a side elevation, partly broken away, of a cartridge similar to that shown in FIGS. 1, 2 and 4, but on a larger scale, and illustrating a piston inserted in the open end of the cartridge and also showing fragmentarily a portion of a plunger rod of the ejector holder adapted to engage the piston of the cartridge.

FIG. 8 is a side elevation of a cartridge similar to FIG. 7, partially showing a cap over the discharge nipple of the cartridge body.

FIG. 9 is a vertical section of the cartridge shown in FIG. 8.

DETAILED DESCRIPTION OF THE PREFERRED EMBODIMENT

Figure 1:
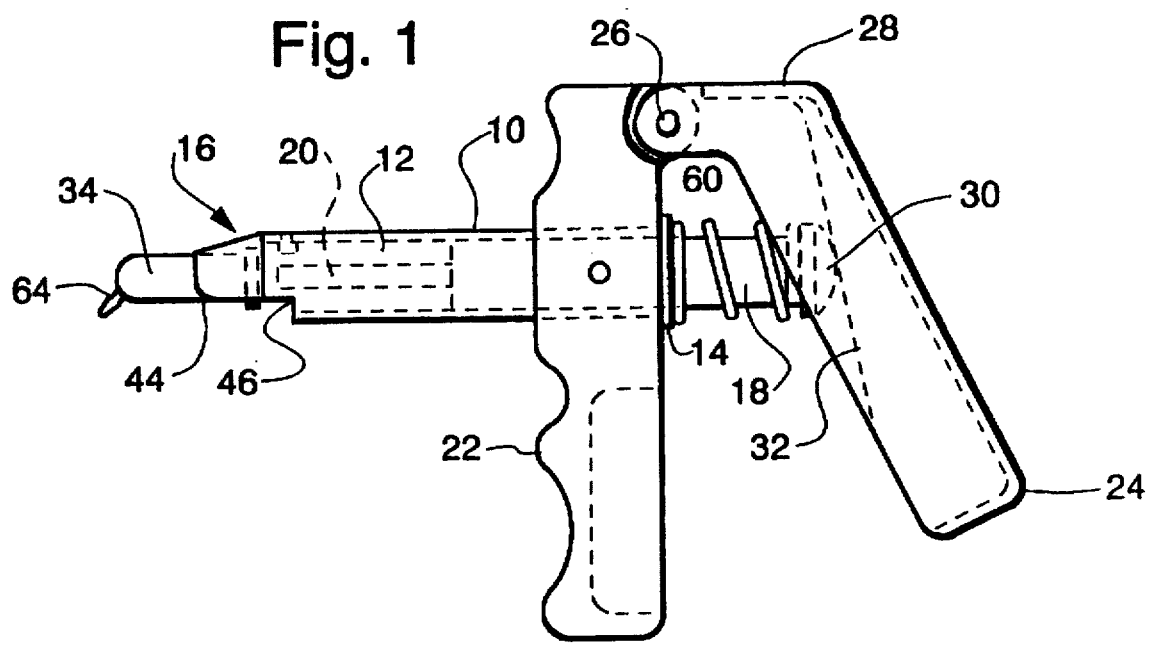
FIG. 1 is a side elevation of an ejector holder for supporting a cartridge in accordance with the present invention.
Figure 6:
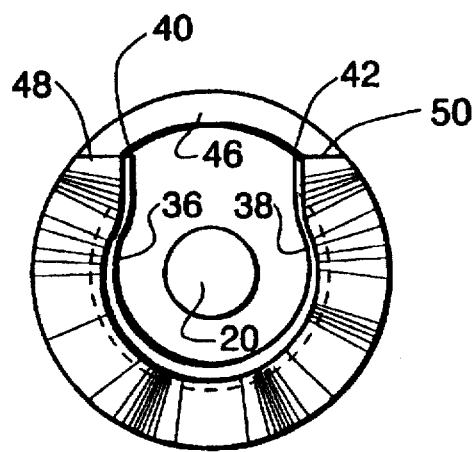
FIG. 6 is a front end view of the forward end of the barrel shown in FIGS. 1–4.

The invention is now described with reference to FIGS. 1–11. FIG. 1 shows an ejector holder of a type especially designed to hold in operative position a cartridge embodying the principles of the present invention. The holder comprises a barrel 10 having a interior bore 12 extending from the rearward end 14 of the barrel toward the forward end 16 thereof for purposes of receiving a plunger 18 of the same diameter as that of the interior bore 12 for the major portion of the length of the plunger, the forward end of the plunger having a smaller diameter extension 20.

Figure 2:
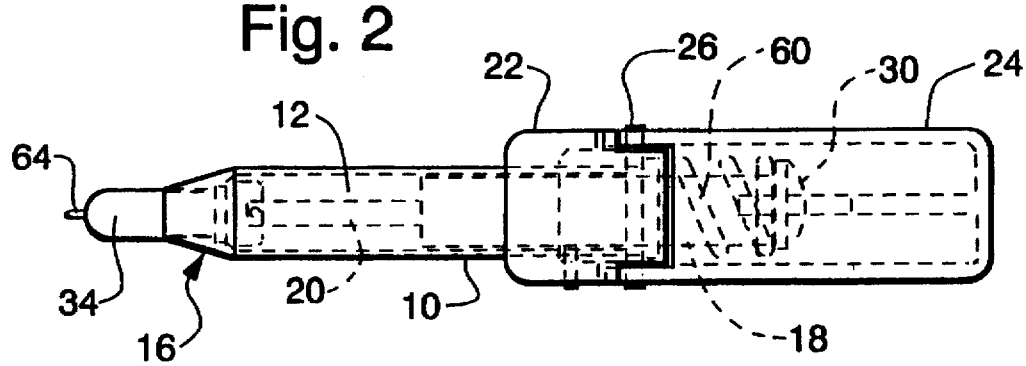
FIG. 2 is a top plan view of the holder and cartridge shown in FIG. 1.

The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26. The upper end 28 of operating lever 24 is offset laterally to facilitate operation of the lever 24 with respect to the outer end of plunger 18 which terminates in a button 30 engageable by the inner surface 32 of operating lever With more particular reference to FIGS. 1–4 it is seen that the forward end 16 of the barrel 10 is tapered and is provided with a longitudinally extending opening comprising compartment 32 which extends rearwardly from the terminal end of the forward end 16 toward the interior bore 12. The lower surface of compartment 32, as viewed in FIG. 3, is semi-cylindrical and is complementary to the elongated body of cartridge 34 so as to receive and seat the same, as shown in FIGS. 1, 2 and 4. However, the sidewalls 36 and 38 of compartment 32 extend upwardly from the semi-cylindrical bottom surface shown in FIG. 3 and are parallel to each other for a limited distance and the upper edges 40 and 42 extend toward each other a limited distance. The Uppermost portions of sidewalls 36 and 38 also have limited flexibility, whereby the distance between the upper edges 40 and 42 of said sidewalls is slightly less than the diameter of the cartridge 34, whereby there is a snap-acting retaining function provided by said sidewalls and the upper edges 40 and 42 with respect to the cartridge 34 when the latter is inserted in the compartment 32.

The forward end 16 of the barrel 10 also has a cutaway portion 44 extending longitudinally rearward to form a shoulder 46, which determines the inner end of the cutaway portion. Due to the fact that the forward end 16 is tapered and the barrel 10 otherwise is circular, the cutaway arrangement provides flat Surfaces 48 and 50. Also, as best shown in FIG. 3, the sidewalls of the compartment 32, at the inner ends thereof, have lateral recesses 52 and 54 which are spaced apart a greater distance than the diameter of the annular exterior flange 56 in order to permit the insertion of the flange into compartment 32 which, following radial insertion movement thereof into the compartment, the cartridge may be moved axially forward for disposition of the flange 56 in an undercut seat 58, which is clearly shown in FIGS. 3–5. The seat, in conjunction with the portion of the compartment 32 extending forwardly therefrom, provides a firm means for supporting a cartridge 34, which is retained seated in the compartment, especially by means of the snap-fitting arrangement provided by the upper edges 40 and 42 of the sidewalls 36 and 38, as described hereinabove.

Without restriction thereto, the preferred material from which the barrel 10, handle member 22 and operating lever 24 are formed is a suitable rigid plastic material in order that these elements may be formed readily and accurately by molding from raw plastic material; obviously, the coiled spring 60 is formed from spring wire for purposes of retracting the plunger 18 when the operating lever 24 is released, following an ejection of material from the cartridge 34.

The cartridge 34 which comprises the subject of the instant application is also preferably formed by molding from appropriate rigid synthetic resin or plastic material by means of a suitable mold. The intermediate body portion of the capsule 34 is of uniform interior and exterior diameter and extends from annular flange 56 adjacent the open end of the cartridge to the opposite closed end 62. The body portion is cylindrical, whereas the closed end 62 is preferably hemi-spherical but is provided with an angularly extending discharge nipple 64, the opening of which is preferably a very fine dimension of small diameter. To effect ejection of material from the cartridge 34, such as dental filling material, cement, or other viscous dental material and the like, for example, the cartridge 34 includes a piston 66, which is very closely complementary in diameter to the interior of the cartridge 34, and the inner end 68 thereof also is hemispherical and complementary to the interior of the closed end 62 of the cartridge. Without restriction thereto, the outer end of the piston may be flat for engagement, for example, with the extension 20, shown fragmentarily in FIG. 7, when the plunger 18 is moved forwardly by actuation of the operating lever 24.

Removal of the capsule 34 from the compartment 32 is accomplished readily by snapping the cartridge outwardly beyond the somewhat flexible upper edges 40 and 42 of the compartment after the contents within the cartridge have been discharged or exhausted, as required.

From the foregoing, it will be seen that the ejector holder is especially adapted to receive the particular type of cartridge to be used therewith, which is the subject of the instant application. The ejector is of very simple, highly effective design, to permit sure and quick mounting of the cartridge within the compartment in the forward end of the barrel of the holder and, with equal facility, removal of the cartridge therefrom is readily achieved.

The cartridge comprising the invention not only is capable of serving as a receptacle for material to be discharged when filled, for example, from a storage supply, but, even more importantly, the cartridge can be filled at a factory with predetermined quantities of material, by automatic machinery, and sealed therein by application of the piston 66, which, under the circumstance, serves as a closure for the cartridge. The above-described design particularly facilitates such operations. Further, during filling, air in the cartridge in advance of the material can be discharged through the nipple 64 until filled and then the open end of the nipple may suitably and inexpensively be closed by suitable seal means, such as a small piece of sheet material having pressure-sensitive cement on one side and fold said piece across the nipple in any suitable manner.

In accordance with the invention, a further improved feature for the cartridge comprises providing a preferably cup-shaped cap 70 which is suitably shaped either to frictionally engage the tip portion of the nipple 64, or either the cap or nipple, or both, to secure the cap releasably upon the tip of the nipple in sealed manner. Cap 70 has outer flange 104 positioned adjacent to the opening of cap 70. In closed position, the inner surface of cap 70 is snap-fit to the outer surface of nipple 64. Cap 70 is retained by the nipple in a closed position, and force sufficient to slightly bend the wall of the cap is required to initially move the cap away from body of cartridge 32 along nipple 64 from the closed position.

Moreover, the cap 70 serves an important additional possible feature in that, in addition to sealing the contents of the cartridge, in conjunction with the piston 66, the cap also may be color-coded for any a number of purposes such as to indicate the kind of material for specified purposes, weight or quantity of the material therein, setting time, and otherwise.

Also, the body of the cartridge as well as the cap 70 and piston 66 may all be molded from similar plastic material which is colored suitably to render the items opaque or otherwise impervious to the transmission of ambient light which, if the contents are subject to being set by such light, prevents premature setting thereof.

Thus, in accordance with a preferred embodiment, the invention provides a miniature capsule-like cartridge having a hollow elongated generally cylindrical body having an inner wall with a substantially uniform diameter. The body has a central axis C as shown in FIG. 9. The inner wall encloses a chamber. One end of the body is open and formed at the extremity thereof with an annular circular exterior flange. The opposite end of the body is closed by an end wall. A discharge integrally connected to the body and has a passageway therethrough extending from the chamber at the closed end of the body to facilitate discharge from the cartridge. The nipple has an outer wall. The outer wall has a proximal diameter 100 proximal to the body and a medial diameter 101 at a position medial to the body. The medial diameter is greater than the proximal diameter. Preferably the proximal diameter is at least 5 percent less than the medial diameter. The nipple has a central axis CN. A cup-shaped cap is removably connected to the discharge nipple on the body to close the outer end of the nipple. The cap extends over the medial position of the nipple.

Figure 10:
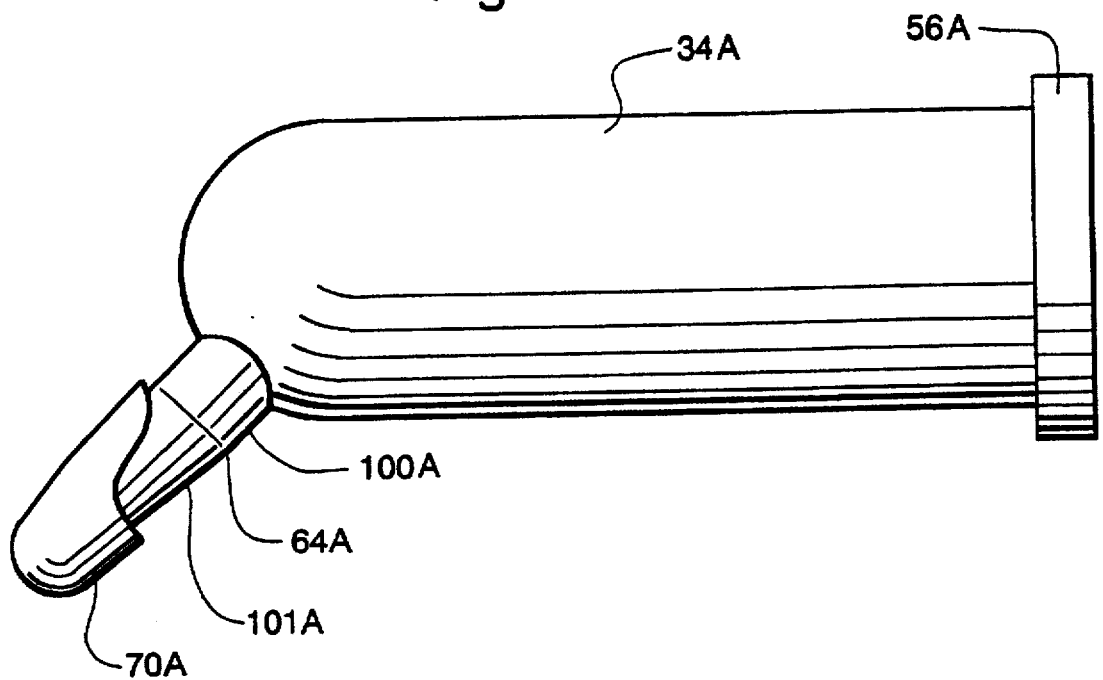
FIG. 10 is a side elevation of a preferred cartridge in accordance with the invention.
Figure 11:
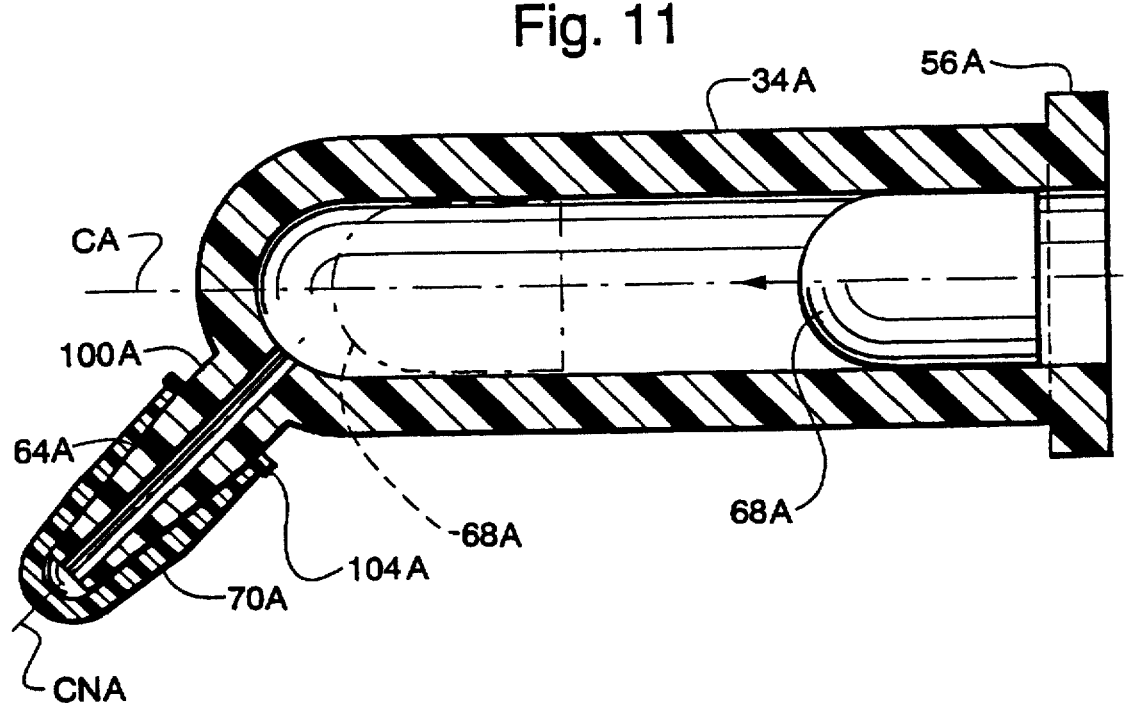
FIG. 11 is a vertical section of the cartridge shown in FIG. 10.

As shown in FIGS. 10 and 11, cartridge 34A in accordance with the invention has a flange 56A and a piston with an inner end 68A. Cartridge 34A is used in the same manner as described above for cartridge 34 with the holder having barrel 10. Preferably cup-shaped cap 70A is suitably shaped either to frictionally engage the tip portion of the nipple 64A, or either the cap or nipple, or both, to secure the cap releasably upon the tip of the nipple in sealed manner. Cap 70A has outer flange 104A positioned adjacent to the opening of cap 70A. In closed position, the inner surface of cap 70A is snap-fit to the outer surface of nipple 64A. Cap 70A is retained by the nipple in a closed position, and force sufficient to slightly bend the wall of the cap is required to initially move the cap away from body of cartridge 34A along nipple 64A from the closed position.

Moreover, the cap 70A serves an important additional possible feature in that, in addition to sealing the contents of the cartridge, in conjunction with the piston, the cap also may be color-coded for any a number of purposes such as to indicate the kind of material for specified purposes, weight or quantity of the material therein, setting time, and otherwise.

Thus, in accordance with a preferred embodiment, the invention provides a miniature capsule-like cartridge having a hollow elongated generally cylindrical body having an inner wall with a substantially uniform diameter. The body has a central axis CA as shown in FIG. 11. The inner wall encloses a chamber. One end of the body is open and formed at the extremity thereof with an annular circular exterior flange. The opposite end of the body is closed by an end wall. A discharge integrally connected to the body and has a passageway therethrough extending from the chamber at the closed end of the body to facilitate discharge from the cartridge. The nipple has a flange 104A and an outer wall. The outer wall has a proximal diameter 100A proximal to the body and a medial diameter 101A at a position medial to the body. The medial diameter is equal to the proximal diameter. The nipple has a central axis CNA. A cup-shaped cap is removably connected to the discharge nipple on the body to close the outer end of the nipple. The cap extends over the medial position of the nipple.

Preferably, the cartridge includes a piston having sidewalls closely complementary to the inner walls of the body and inserted into the open end thereof. The inner end of the piston is complementary in shape to the interior surface of the closed end of the body. Preferably the cap has an inner wall, and the inner wall of the cap engages the outer wall of the nipple at the medial portion of the nipple. Preferably the body has a planar surface positioned adjacent to the closed end and opposite to the nipple and the planar surface intersects the end wall along a line which forms an acute angle to the central axis of the body. Preferably the acute angle is between 3 degrees and 25 degrees.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

What is claimed is:

1. A miniature capsule-like cartridge, comprising:

a hollow elongated uniformly cylindrical body of predetermined length and uniform diameter interiorly and exteriorly and molded from rigid plastic material, one end of said body being open and formed at the extremity thereof with an annular relatively short circular exterior flange of limited width and adapted to be detachably mounted within a complementary seat in an ejector type holder, the opposite end of said body being closed by a wall of substantially the same uniform thickness as said body, a discharge nipple of the same material as the body and molded integrally therewith and having a passage therethrough extending from said closed end of said body to facilitate directing discharge from the cartridge to the interior of an oral cavity, said nipple having a wall, said wall having an outer surface with a proximal diameter proximal to said body and a medial diameter medial to said body, said medial diameter being substantially equal to said proximal diameter, a piston having sidewalls closely complementary to the inner walls of said body and inserted into the open end thereof to form a combination closure and ejecting means for material when contained in said cartridge, the inner end of said piston being hemispherical and complementary in shape to the interior surface of the closed end of said body to effect ejection of substantially the entire contents of said cartridge when said piston is fully inserted into said body of the cartridge, and sealing means comprising a cup-shaped cap removably connected to the discharge nipple on said body to close said outer end of the nipple to seal the contents of the cartridge against ingress of ambient atmosphere and/or any surrounding contaminating matter.

2. The cartridge according to claim 1 further characterized by said body and piston being formed from plastic material suitably colored to render the same impervious to the transmission of ambient light, thereby rendering the cartridge adapted to contain light-curable material and the like in a manner to prevent premature curing of such material while stored in such cartridge.

3. The cartridge of claim 1 wherein said cap is color-coded to indicate desired properties of the contents of the cartridge.

4. The cartridge of claim 1 wherein said nipple outer wall has a distal diameter, and said medial diameter is greater than said distal diameter.

5. The cartridge of claim 1 wherein said body has a flat portion opposite to said nipple and adjacent to said closed end.

6. A miniature capsule-like cartridge, comprising:

a hollow elongated generally cylindrical body having an inner wall with a substantially uniform diameter, said inner wall enclosing a chamber, said chamber enclosing viscous polymerizable dental material, one end of said body being open and formed at the extremity thereof with an annular circular exterior flange, the opposite end of said body being closed by an end wall, a discharge nipple integrally connected to said body and having a passageway therethrough extending from said chamber at said closed end of said body to facilitate discharge from the cartridge, said nipple having a wall, said wall having an outer surface with a proximal diameter proximal to said body and a medial diameter at a medial position along the central axis of said nipple and medial to said body, said medial diameter being greater than said proximal diameter, and a cup-shaped cap removably connected to the discharge nipple on said body to close said outer end of the nipple to seal, said cap extending over said medial position of said nipple, said cap having an outer flange and an inner surface, said inner surface of said cap being fit to the outer surface of said nipple, whereby a force sufficient to slightly bend said wall of the cap being required to initially move the cap away from said body along said nipple.

7. The cartridge of claim 6 further comprising a piston having sidewalls closely complementary to the inner walls of said body and inserted into the open end thereof, the inner end of said piston being complementary in shape to the interior surface of the closed end of said body.

8. The cartridge of claim 6 wherein said cap has an inner wall, and said inner wall of said cap engages said outer wall of said nipple at said medial position of said nipple.

9. The cartridge of claim 1 wherein said body encloses a polymerizable dental composition.

10. The cartridge of claim 1 wherein said cap has an outer flange.

11. The cartridge of claim 1 wherein said cap has an inner surface, and said inner surface of said cap is snap-fit to said outer surface of said nipple.

12. The cartridge of claim 1 wherein said cap is retained by said nipple in a closed position, and force sufficient to slightly bend said wall of said cap is required to initially move said cap away from said body along said nipple.

* * * * *